United States Patent
Zammataro

(10) Patent No.: US 9,186,153 B2
(45) Date of Patent: Nov. 17, 2015

(54) LOCKING CAM DRIVER AND JAW ASSEMBLY FOR CLIP APPLIER

(75) Inventor: Tom Zammataro, Hamden, CT (US)

(73) Assignee: Covidien LP, Mansfield, MA (US)

( * ) Notice: Subject to any disclaimer, the term of this patent is extended or adjusted under 35 U.S.C. 154(b) by 1021 days.

(21) Appl. No.: 13/303,335

(22) Filed: Nov. 23, 2011

(65) Prior Publication Data

US 2012/0197269 A1    Aug. 2, 2012

Related U.S. Application Data

(60) Provisional application No. 61/438,086, filed on Jan. 31, 2011.

(51) Int. Cl.
*A61B 17/10* (2006.01)
*A61B 17/128* (2006.01)
*A61B 17/122* (2006.01)

(52) U.S. Cl.
CPC ............ *A61B 17/1285* (2013.01); *A61B 17/122* (2013.01)

(58) Field of Classification Search
CPC ............. A61B 17/1285; A61B 17/122; A61B 17/128; A61B 2019/304; A61B 17/10
USPC ............... 606/139, 142, 143; 6/139, 142, 143
See application file for complete search history.

(56) References Cited

U.S. PATENT DOCUMENTS

| | | |
|---|---|---|
| 3,120,230 A | 2/1964 | Skold |
| 3,638,847 A | 2/1972 | Noiles et al. |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |

(Continued)

FOREIGN PATENT DOCUMENTS

| | | |
|---|---|---|
| DE | 20 2009 00611 | 7/2009 |
| EP | 0 085 931 A2 | 8/1983 |

(Continued)

OTHER PUBLICATIONS

Extended European Search Report corresponding to EP 13 16 6382.5, completed Nov. 19, 2013 and mailed Nov. 28, 2013; (8 pp).

(Continued)

*Primary Examiner* — Victor Nguyen
*Assistant Examiner* — Kevin Everage

(57) ABSTRACT

The present disclosure relates to an apparatus for endoscopic application of surgical clips to body tissue. The apparatus includes a handle portion, an elongated tubular member, one or more surgical clips, a jaw assembly and a locking cam driver. The elongated tubular member extends distally from the handle portion and defines a longitudinal axis. The surgical clips are disposed within the tubular member. The locking cam driver includes a bifurcated distal end portion that has a pair of angled camming surfaces to facilitate closure of the jaw assembly.

15 Claims, 7 Drawing Sheets

(56) References Cited

U.S. PATENT DOCUMENTS

| | | |
|---|---|---|
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry |
| 5,382,255 A | 1/1995 | Castro |
| 5,383,881 A | 1/1995 | Green |
| 5,395,375 A | 3/1995 | Turkel et al. |
| 5,395,381 A | 3/1995 | Green |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green |
| 5,425,740 A | 6/1995 | Hutchinson, Jr. |
| 5,431,667 A | 7/1995 | Thompson |
| 5,431,668 A | 7/1995 | Burbank, III et al. |
| 5,431,669 A | 7/1995 | Thompson |
| 5,439,468 A | 8/1995 | Schulze et al. |
| 5,441,509 A | 8/1995 | Vidal |
| 5,447,513 A | 9/1995 | Davison et al. |
| 5,449,365 A | 9/1995 | Green |
| 5,462,555 A | 10/1995 | Bolanos |
| 5,462,558 A | 10/1995 | Kolesa |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |

(56) References Cited

U.S. PATENT DOCUMENTS

| | | |
|---|---|---|
| 5,509,920 A | 4/1996 | Phillips |
| 5,514,149 A | 5/1996 | Green |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green |
| 5,527,320 A | 6/1996 | Carruthers et al. |
| 5,542,949 A | 8/1996 | Yoon |
| 5,547,474 A | 8/1996 | Kloeckl |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt |
| 5,618,291 A | 4/1997 | Thompson |
| 5,618,306 A | 4/1997 | Roth et al. |
| 5,620,452 A | 4/1997 | Yoon |
| 5,626,585 A | 5/1997 | Mittelstadt |
| 5,626,586 A | 5/1997 | Pistl et al. |
| 5,626,592 A | 5/1997 | Phillips |
| RE35,525 E | 6/1997 | Stefanchik et al. |
| 5,634,930 A | 6/1997 | Thornton et al. |
| 5,643,291 A | 7/1997 | Pier |
| 5,645,551 A | 7/1997 | Green |
| 5,645,553 A | 7/1997 | Kolesa |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier |
| 5,695,505 A | 12/1997 | Yoon |
| 5,697,938 A | 12/1997 | Jensen et al. |
| 5,700,270 A | 12/1997 | Peyser |
| 5,700,271 A | 12/1997 | Whitfield |
| 5,702,048 A | 12/1997 | Eberlin |
| 5,709,706 A | 1/1998 | Kienzle et al. |
| 5,713,911 A | 2/1998 | Racenet |
| 5,713,912 A | 2/1998 | Porter |
| 5,720,756 A | 2/1998 | Green |
| 5,722,982 A | 3/1998 | Ferreira et al. |
| 5,725,537 A | 3/1998 | Green |
| 5,725,538 A | 3/1998 | Green |
| 5,725,542 A | 3/1998 | Yoon |
| 5,733,295 A | 3/1998 | Back et al. |
| 5,755,726 A | 5/1998 | Pratt |
| 5,766,189 A | 6/1998 | Matsuno |
| 5,769,857 A | 6/1998 | Reztzov et al. |
| 5,772,673 A | 6/1998 | Cuny |
| 5,776,146 A | 7/1998 | Sackier et al. |
| 5,776,147 A | 7/1998 | Dolendo |
| 5,779,718 A | 7/1998 | Green |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts |
| 5,792,150 A | 8/1998 | Pratt |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield |
| 5,833,700 A | 11/1998 | Fogelberg et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser |
| 5,868,761 A | 2/1999 | Nicholas |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser |
| 5,951,574 A | 9/1999 | Stefanchik et al. |
| 5,972,003 A | 10/1999 | Rousseau |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,045,560 A | 4/2000 | McKean et al. |
| RE36,720 E | 5/2000 | Green |
| 6,059,799 A | 5/2000 | Aranyi |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis |
| 6,537,289 B1 | 3/2003 | Kayan |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan |
| 6,676,659 B2 | 1/2004 | Hutchins et al. |
| 6,679,894 B2 | 1/2004 | Damarati |
| RE38,445 E | 2/2004 | Pistl |
| 6,695,854 B1 | 2/2004 | Kayan |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |

(56) References Cited

U.S. PATENT DOCUMENTS

| | | |
|---|---|---|
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,637,917 B2 | 12/2009 | Whitfield |
| 7,695,482 B2 | 4/2010 | Viola |
| 7,717,926 B2 | 5/2010 | Whitfield |
| 7,727,248 B2 | 6/2010 | Smith et al. |
| 7,819,886 B2 | 10/2010 | Whitfield |
| 7,887,553 B2 | 2/2011 | Lehman et al. |
| 7,905,890 B2 | 3/2011 | Whitfield |
| 7,942,885 B2 | 5/2011 | Sixto, Jr. et al. |
| 7,988,027 B2 | 8/2011 | Olson |
| 8,011,550 B2 | 9/2011 | Aranyi |
| 8,011,555 B2 | 9/2011 | Tarinelli |
| 8,016,178 B2 | 9/2011 | Olson |
| 8,021,375 B2 | 9/2011 | Aldrich |
| 8,021,378 B2 | 9/2011 | Sixto, Jr. |
| 8,056,565 B2 | 11/2011 | Zergiebel |
| 8,062,310 B2 | 11/2011 | Shibata et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,080,021 B2 | 12/2011 | Griego |
| 8,083,668 B2 | 12/2011 | Durgin |
| 8,088,061 B2 | 1/2012 | Wells |
| 8,091,755 B2 | 1/2012 | Kayan |
| 8,100,926 B1 | 1/2012 | Filshie et al. |
| 8,128,643 B2 | 3/2012 | Aranyi |
| 8,142,451 B2 | 3/2012 | Boulnois |
| 8,157,149 B2 | 4/2012 | Olson |
| 8,157,151 B2 | 4/2012 | Ingmanson |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema |
| 8,236,012 B2 | 8/2012 | Molitor |
| 8,246,634 B2 | 8/2012 | Huitema |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,282,655 B2 | 10/2012 | Whitfield |
| 8,308,743 B2 | 11/2012 | Matsuno et al. |
| 8,328,822 B2 | 12/2012 | Huitema |
| 8,336,556 B2 | 12/2012 | Zergiebel |
| 8,348,130 B2 | 1/2013 | Shah |
| 8,357,171 B2 | 1/2013 | Whitfield |
| 8,366,726 B2 | 2/2013 | Dennis |
| 8,371,491 B2 | 2/2013 | Huitema |
| 8,372,095 B2 | 2/2013 | Viola |
| 8,382,773 B2 | 2/2013 | Whitfield |
| 8,398,655 B2 | 3/2013 | Cheng et al. |
| 8,403,945 B2 | 3/2013 | Whitfield |
| 8,403,946 B2 | 3/2013 | Whitfield |
| 8,409,222 B2 | 4/2013 | Whitfield |
| 8,409,223 B2 | 4/2013 | Sorrentino |
| 8,419,752 B2 | 4/2013 | Sorrentino |
| 8,430,892 B2 | 4/2013 | Bindra |
| 8,444,660 B2 | 5/2013 | Adams |
| 8,465,502 B2 | 6/2013 | Zergiebel |
| 8,475,473 B2 | 7/2013 | Vandenbroek |
| 8,480,688 B2 | 7/2013 | Boulnois |
| 8,486,091 B2 | 7/2013 | Sorrentino |
| 8,491,608 B2 | 7/2013 | Sorrentino |
| 8,496,673 B2 | 7/2013 | Nguyen |
| 8,506,580 B2 | 8/2013 | Zergiebel |
| 8,512,357 B2 | 8/2013 | Viola |

(56) References Cited

U.S. PATENT DOCUMENTS

| | | | |
|---|---|---|---|
| 8,523,882 B2 | 9/2013 | Huitema | |
| 8,529,585 B2 | 9/2013 | Jacobs | |
| 8,529,586 B2 | 9/2013 | Rosenberg | |
| 8,529,588 B2 | 9/2013 | Ahlberg | |
| 8,545,486 B2 | 10/2013 | Malkowski | |
| 8,556,920 B2 | 10/2013 | Huitema et al. | |
| 8,568,430 B2 | 10/2013 | Shipp | |
| 8,579,918 B2 | 11/2013 | Whitfield | |
| 8,585,717 B2 | 11/2013 | Sorrentino | |
| 8,603,109 B2 | 12/2013 | Aranyi | |
| 8,609,109 B2 | 12/2013 | Aranyi | |
| 8,652,151 B2 | 2/2014 | Lehman et al. | |
| 8,652,152 B2 | 2/2014 | Aranyi et al. | |
| 8,663,247 B2 | 3/2014 | Menn et al. | |
| 8,685,048 B2 | 4/2014 | Adams et al. | |
| 8,690,899 B2 | 4/2014 | Kogiso et al. | |
| 8,709,027 B2 | 4/2014 | Adams et al. | |
| 8,734,469 B2 | 5/2014 | Pribanic et al. | |
| 8,747,423 B2 | 6/2014 | Whitfield et al. | |
| 8,753,356 B2 | 6/2014 | Vitali et al. | |
| 8,814,884 B2 | 8/2014 | Whitfield et al. | |
| 8,821,516 B2 | 9/2014 | Huitema | |
| 8,839,954 B2 | 9/2014 | Disch | |
| 8,845,659 B2 | 9/2014 | Whitfield et al. | |
| 8,894,665 B2 | 11/2014 | Sorrentino et al. | |
| 8,894,666 B2 | 11/2014 | Schulz et al. | |
| 8,920,438 B2 | 12/2014 | Aranyi et al. | |
| 2001/0047178 A1 | 11/2001 | Peters | |
| 2002/0068947 A1 | 6/2002 | Kuhns et al. | |
| 2002/0082618 A1 | 6/2002 | Shipp et al. | |
| 2002/0087169 A1 | 7/2002 | Brock et al. | |
| 2002/0087170 A1 | 7/2002 | Kuhns et al. | |
| 2002/0099388 A1 | 7/2002 | Mayenberger | |
| 2002/0120279 A1 | 8/2002 | Deguillebon et al. | |
| 2002/0128668 A1 | 9/2002 | Manetakis et al. | |
| 2002/0177859 A1 | 11/2002 | Monassevitch et al. | |
| 2002/0198537 A1 | 12/2002 | Smith et al. | |
| 2002/0198538 A1 | 12/2002 | Kortenbach et al. | |
| 2002/0198539 A1 | 12/2002 | Sixto, Jr. et al. | |
| 2002/0198540 A1 | 12/2002 | Smith et al. | |
| 2002/0198541 A1 | 12/2002 | Smith et al. | |
| 2003/0014060 A1 | 1/2003 | Wilson, Jr. et al. | |
| 2003/0018345 A1 | 1/2003 | Green | |
| 2003/0023249 A1 | 1/2003 | Manetakis | |
| 2003/0040759 A1 | 2/2003 | de Guillebon et al. | |
| 2003/0105476 A1 | 6/2003 | Sancoff et al. | |
| 2003/0114867 A1 | 6/2003 | Bolduc et al. | |
| 2003/0135224 A1 | 7/2003 | Blake, III | |
| 2003/0167063 A1 | 9/2003 | Kerr | |
| 2003/0208231 A1 | 11/2003 | Williamson, IV et al. | |
| 2003/0225423 A1 | 12/2003 | Huitema | |
| 2003/0233105 A1 | 12/2003 | Gayton | |
| 2004/0010272 A1 | 1/2004 | Manetakis et al. | |
| 2004/0097970 A1 | 5/2004 | Hughett | |
| 2004/0097971 A1 | 5/2004 | Hughett | |
| 2004/0138681 A1 | 7/2004 | Pier | |
| 2004/0153100 A1 | 8/2004 | Ahlberg et al. | |
| 2004/0193213 A1 | 9/2004 | Aranyi | |
| 2005/0080440 A1 | 4/2005 | Durgin et al. | |
| 2005/0085830 A1 | 4/2005 | Lehman et al. | |
| 2005/0090837 A1 | 4/2005 | Sixto, Jr. et al. | |
| 2005/0090838 A1 | 4/2005 | Sixto, Jr. et al. | |
| 2005/0096670 A1 | 5/2005 | Wellman et al. | |
| 2005/0096671 A1 | 5/2005 | Wellman et al. | |
| 2005/0096672 A1 | 5/2005 | Manetakis et al. | |
| 2005/0101975 A1 | 5/2005 | Nguyen et al. | |
| 2005/0107807 A1 | 5/2005 | Nakao | |
| 2005/0107809 A1 | 5/2005 | Litscher et al. | |
| 2005/0107810 A1 | 5/2005 | Morales et al. | |
| 2005/0107811 A1 | 5/2005 | Starksen et al. | |
| 2005/0107812 A1 | 5/2005 | Starksen et al. | |
| 2005/0107871 A1 | 5/2005 | Realyvasquez et al. | |
| 2005/0113847 A1 | 5/2005 | Gadberry et al. | |
| 2005/0119671 A1 | 6/2005 | Reydel et al. | |
| 2005/0119673 A1 | 6/2005 | Gordon et al. | |
| 2005/0119677 A1 | 6/2005 | Shipp | |
| 2005/0125010 A1 | 6/2005 | Smith et al. | |
| 2005/0143767 A1 | 6/2005 | Kimura et al. | |
| 2005/0149063 A1 | 7/2005 | Young et al. | |
| 2005/0149064 A1 | 7/2005 | Peterson et al. | |
| 2005/0149068 A1 | 7/2005 | Williams et al. | |
| 2005/0149069 A1 | 7/2005 | Bertolero et al. | |
| 2005/0165415 A1 | 7/2005 | Wales | |
| 2005/0165418 A1 | 7/2005 | Chan | |
| 2005/0171560 A1 | 8/2005 | Hughett | |
| 2005/0175703 A1 | 8/2005 | Hunter | |
| 2005/0177176 A1 | 8/2005 | Gerbi et al. | |
| 2005/0177177 A1 | 8/2005 | Viola | |
| 2005/0203547 A1 | 9/2005 | Weller et al. | |
| 2005/0203548 A1 | 9/2005 | Weller et al. | |
| 2005/0216036 A1 | 9/2005 | Nakao | |
| 2005/0216056 A1 | 9/2005 | Valdevit et al. | |
| 2005/0222588 A1 | 10/2005 | Vandenbroek et al. | |
| 2005/0222590 A1 | 10/2005 | Gadberry et al. | |
| 2005/0222665 A1 | 10/2005 | Aranyi | |
| 2005/0228411 A1 | 10/2005 | Manzo | |
| 2005/0228416 A1 | 10/2005 | Burbank et al. | |
| 2005/0234478 A1 | 10/2005 | Wixey et al. | |
| 2005/0251183 A1 | 11/2005 | Buckman et al. | |
| 2005/0251184 A1 | 11/2005 | Anderson | |
| 2005/0256529 A1 | 11/2005 | Yawata et al. | |
| 2005/0267495 A1 | 12/2005 | Ginn et al. | |
| 2005/0273122 A1 | 12/2005 | Theroux et al. | |
| 2005/0277951 A1 | 12/2005 | Smith et al. | |
| 2005/0277952 A1 | 12/2005 | Arp et al. | |
| 2005/0277953 A1 | 12/2005 | Francese et al. | |
| 2005/0277954 A1 | 12/2005 | Smith et al. | |
| 2005/0277955 A1 | 12/2005 | Palmer et al. | |
| 2005/0277956 A1 | 12/2005 | Francese et al. | |
| 2005/0277958 A1 | 12/2005 | Levinson | |
| 2005/0288689 A1 | 12/2005 | Kammerer et al. | |
| 2005/0288690 A1 | 12/2005 | Bourque et al. | |
| 2006/0004388 A1 | 1/2006 | Whayne et al. | |
| 2006/0004390 A1 | 1/2006 | Rosenberg et al. | |
| 2006/0009789 A1 | 1/2006 | Gambale et al. | |
| 2006/0009790 A1 | 1/2006 | Blake, III et al. | |
| 2006/0009792 A1 | 1/2006 | Baker et al. | |
| 2006/0020270 A1 | 1/2006 | Jabba et al. | |
| 2006/0020271 A1 | 1/2006 | Stewart et al. | |
| 2006/0047305 A1 | 3/2006 | Ortiz et al. | |
| 2006/0047306 A1 | 3/2006 | Ortiz et al. | |
| 2006/0064117 A1 | 3/2006 | Aranyi et al. | |
| 2006/0079115 A1 | 4/2006 | Aranyi | |
| 2006/0079912 A1 | 4/2006 | Whitfield et al. | |
| 2006/0079913 A1* | 4/2006 | Whitfield | A61B 17/10 606/142 |
| 2006/0085015 A1 | 4/2006 | Whitfield et al. | |
| 2006/0100649 A1 | 5/2006 | Hart | |
| 2006/0111731 A1 | 5/2006 | Manzo | |
| 2006/0129170 A1 | 6/2006 | Royce et al. | |
| 2006/0163312 A1 | 7/2006 | Viola et al. | |
| 2006/0173470 A1 | 8/2006 | Oray et al. | |
| 2006/0178683 A1 | 8/2006 | Shimoji et al. | |
| 2006/0184182 A1 | 8/2006 | Aranyi et al. | |
| 2006/0190013 A1 | 8/2006 | Menn | |
| 2006/0195125 A1 | 8/2006 | Sakakine et al. | |
| 2006/0200179 A1 | 9/2006 | Barker et al. | |
| 2006/0217749 A1 | 9/2006 | Wilson, Jr. et al. | |
| 2006/0224170 A1 | 10/2006 | Duff | |
| 2006/0235437 A1 | 10/2006 | Vitali et al. | |
| 2006/0235438 A1 | 10/2006 | Huitema et al. | |
| 2006/0235439 A1 | 10/2006 | Molitor et al. | |
| 2006/0235440 A1 | 10/2006 | Huitema et al. | |
| 2006/0235441 A1 | 10/2006 | Huitema et al. | |
| 2006/0235442 A1 | 10/2006 | Huitema | |
| 2006/0235443 A1 | 10/2006 | Huitema et al. | |
| 2006/0235444 A1 | 10/2006 | Huitema et al. | |
| 2006/0259045 A1 | 11/2006 | Damarati | |
| 2006/0259049 A1 | 11/2006 | Harada et al. | |
| 2006/0264987 A1 | 11/2006 | Sgro | |
| 2006/0271072 A1 | 11/2006 | Hummel et al. | |
| 2007/0016228 A1 | 1/2007 | Salas | |
| 2007/0021761 A1 | 1/2007 | Phillips | |
| 2007/0023476 A1 | 2/2007 | Whitman et al. | |

(56) References Cited

U.S. PATENT DOCUMENTS

| | | |
|---|---|---|
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0243145 A1 | 10/2008 | Whitfield et al. |
| 2010/0057105 A1 | 3/2010 | Sorrentino |
| 2010/0057107 A1 | 3/2010 | Sorrentino |
| 2010/0274262 A1 | 10/2010 | Schulz et al. |
| 2010/0274264 A1 | 10/2010 | Schulz et al. |
| 2011/0087242 A1 | 4/2011 | Pribanic |
| 2011/0137323 A1 | 6/2011 | Malkowski |
| 2011/0208212 A1 | 8/2011 | Zergiebel |
| 2011/0224701 A1 | 9/2011 | Menn |
| 2011/0245847 A1 | 10/2011 | Menn |
| 2012/0029534 A1 | 2/2012 | Whitfield |
| 2012/0109158 A1 | 5/2012 | Zammataro |
| 2012/0116420 A1 | 5/2012 | Sorrentino |
| 2012/0123446 A1 | 5/2012 | Aranyi |
| 2012/0197269 A1 | 8/2012 | Zammataro |
| 2012/0265220 A1 | 10/2012 | Menn |
| 2012/0277765 A1 | 11/2012 | Zammataro |
| 2012/0330326 A1 | 12/2012 | Creston |
| 2013/0110135 A1 | 5/2013 | Whitfield |
| 2013/0131697 A1 | 5/2013 | Hartoumbekis |
| 2013/0165952 A1 | 6/2013 | Whitfield |
| 2013/0172910 A1 | 7/2013 | Malkowski |
| 2013/0172911 A1 | 7/2013 | Rockrohr |
| 2013/0172912 A1 | 7/2013 | Whitfield |
| 2013/0190779 A1 | 7/2013 | Whitfield |
| 2013/0190780 A1 | 7/2013 | Whitfield |
| 2013/0253541 A1 | 9/2013 | Zergiebel |
| 2013/0274767 A1 | 10/2013 | Sorrentino |
| 2013/0289583 A1 | 10/2013 | Zergiebel |
| 2013/0296891 A1 | 11/2013 | Hartoumbekis |
| 2013/0296892 A1 | 11/2013 | Sorrentino |
| 2013/0310849 A1 | 11/2013 | Malkowski |
| 2013/0325040 A1 | 12/2013 | Zammataro |
| 2014/0039526 A1 | 2/2014 | Malkowski |
| 2014/0052157 A1 | 2/2014 | Whitfield |
| 2014/0058412 A1 | 2/2014 | Aranyi |
| 2014/0194903 A1 | 7/2014 | Malkowski et al. |
| 2014/0207156 A1 | 7/2014 | Malkowski |
| 2014/0316441 A1 | 10/2014 | Zergiebel et al. |
| 2015/0005790 A1 | 1/2015 | Whitfield et al. |

FOREIGN PATENT DOCUMENTS

| | | |
|---|---|---|
| EP | 0 086 721 | 8/1983 |
| EP | 0 089 737 A1 | 9/1983 |
| EP | 0 324 166 A2 | 7/1989 |
| EP | 0 392 750 A1 | 10/1990 |
| EP | 0 409 569 A1 | 1/1991 |
| EP | 0 569 223 | 11/1993 |
| EP | 0 594 003 | 4/1994 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 | 4/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 | 12/2005 |
| EP | 1 712 187 | 10/2006 |
| EP | 1 712 191 A2 | 10/2006 |
| EP | 1 757 236 | 2/2007 |
| EP | 1 813 199 A1 | 8/2007 |
| EP | 1 908 423 | 4/2008 |
| EP | 1 908 423 A2 | 4/2008 |
| EP | 1 913 881 A1 | 4/2008 |
| EP | 2 229 895 A1 | 9/2010 |
| EP | 2 332 471 | 6/2011 |
| JP | 2003 033361 A | 2/2003 |
| WO | WO 01/66001 | 9/2001 |
| WO | WO 01/67965 | 9/2001 |
| WO | WO 03/086207 | 10/2003 |
| WO | WO 03/092473 | 11/2003 |
| WO | WO 2005/091457 | 9/2005 |
| WO | WO 2006/042076 | 4/2006 |
| WO | WO 2006/042076 A2 | 4/2006 |
| WO | WO 2006/042084 A2 | 4/2006 |
| WO | WO 2006/042110 | 4/2006 |
| WO | WO 2006/042110 A2 | 4/2006 |
| WO | WO 2006/042141 | 4/2006 |
| WO | WO 2006/135479 | 12/2006 |
| WO | WO 2008/118928 | 10/2008 |
| WO | WO 2008/118928 A2 | 10/2008 |
| WO | WO 2008/127968 | 10/2008 |
| WO | WO 2008/127968 A2 | 10/2008 |

OTHER PUBLICATIONS

Extended European Search Report corresponding to EP 11 25 0194.5, completed Nov. 25, 2013 and mailed Dec. 3, 2013; (8 pp).

Extended European Search Report corresponding to EP 10 25 1798.4, completed Dec. 12, 2013 and mailed Jan. 2, 2014; (9 pp).

European Search Report corresponding to European Application No. EP 05 80 2686.5, completed Jan. 9, 2012; mailed Jan. 18, 2012; (3 Pages).

The extended European Search Report corresponding to European Application No. EP 12 15 1313.9, completed Mar. 20, 2012 and mailed Apr. 12, 2012; (5 Pages).

The extended European Search Report corresponding to European Application No. EP 12 16 1291.5, completed Apr. 24, 2012 and mailed May 4, 2012; (5 Pages).

The extended European Search Report corresponding to European Application No. EP 12 16 2288.0, completed Jun. 4, 2012 and mailed Jul. 7, 2012; (6 Pages).

The extended European Search Report corresponding to European Application No. EP 12 16 5891.8, completed Jun. 12, 2012 and mailed Jun. 20, 2012; (6 Pages).

(56) References Cited

OTHER PUBLICATIONS

The extended European Search Report corresponding to European Application No. EP 12 16 4955.2, completed Aug. 23, 2012 and mailed Sep. 4, 2012; (5 Pages).
Extended European Search Report corresponding to EP 12 19 8745.7, completed Mar. 19, 2013 and mailed Apr. 11, 2013; (8 pp).
Extended European Search Report corresponding to EP 08 73 2820.9, completed Jul. 2, 2013 and mailed Jul. 9, 2013; (10 pp).
Extended European Search Report corresponding to EP 12 19 1706.6, completed Dec. 19, 2012 and mailed Jan. 8, 2013; (6 pp).
Extended European Search Report corresponding to EP 13 17 2008.8, completed Aug. 14, 2013 and mailed Aug. 28, 2013; (8 pp).
Extended European Search Report corresponding to EP 12 15 2989.5, completed Apr. 9, 2013 and mailed Apr. 18, 2013; (9 pp).
Extended European Search Report corresponding to EP 10 25 2112.7, completed Jul. 29, 2014 and mailed Aug. 5, 2014; (8 pp).
Extended European Search Report corresponding to EP 14 15 1673.2, completed Apr. 25, 2014 and mailed May 8, 2014; (8 pp).
The extended International Search Report corresponding to European Application No. 07 25 3905.9, completed Jan. 29, 2008; mailed Feb. 7, 2008; (7 Pages).
The partial International Search Report corresponding to European Application No. EP 07 25 3807.7, completed Jul. 23, 2008; mailed Aug. 1, 2008; (3 pages).
International Search Report corresponding to International Application No. PCT/US08/58185, completed Sep. 4, 2008; mailed Sep. 9, 2008; (2 Pages).
The International Search Report corresponding to International Application No. PCT/US08/59859, completed Sep. 14, 2008; mailed Sep. 18. 2008; (2 Pages).
The extended European Search Report corresponding to European Application No. EP 07 25 3807.7, completed Nov. 7, 2008; mailed Nov. 26, 2008; (11 Pages).
The extended European Search Report corresponding to European Application No. EP 09252049.3, completed Dec. 11, 2009: mailed Jan. 12, 2010; (3 Pages).
The extended European Search Report corresponding to European Application No. EP 09252050.1, completed Dec. 23, 2009; mailed Jan. 21, 2010; (3 Pages).
The extended European Search Report corresponding to European Application No. EP 09252051.9, completed Dec. 21, 2009; mailed Jan. 28, 2010; (3 Pages).
The extended European Search Report corresponding to European Application No. EP 09252052.7. completed Nov. 16, 2009; mailed Nov. 24, 2009; (3 Pages).
The extended European Search Report corresponding to European Application No. EP 09252053.5, completed Nov. 24, 2009; mailed Dec. 1, 2009; (3 Pages).
The extended European Search Report corresponding to European Application No. EP 09252054.3, completed Jan. 7, 2010; mailed Jan. 22, 2010; (3 Pages).
Extended European Search Report corresponding to European Application No. EP 09252056.8, completed Jan. 8, 2010; mailed Feb. 5, 2010; (3 Pages).
Extended European Search Report corresponding to European Application No. EP 10250497.4, completed May 4, 2010; mailed May 12, 2010; (6 Pages).
Extended European Search Report corresponding to European Application No. EP 10252079.8, completed Mar. 8, 2011; mailed Mar. 17, 2011; (3 Pages).
European Search Report corresponding to European Application No. EP 05810218.7, completed Apr. 18, 2011; mailed May 20, 2011; (3 pages).
European Search Report corresponding to European Application No. EP 05807612.6, completed May 2, 2011; mailed May 20, 2011; (3 pages).
Extended European Search Report corresponding to European Application No. EP 10251737.2, completed May 9, 2011; mailed May 20, 2011; (4 pages).
Extended European Search Report corresponding to European Application No. EP 11002681.2, completed May 31, 2011; mailed Jun. 10, 2011; (3 Pages).
The extended European Search Report corresponding to European Application No. EP 11250214.1, completed May 25, 2011; mailed Jun. 1, 2011; (3 Pages).
"Salute II Disposable Fixation Device", Technique Guide—Laparoscopic and Open Inguinal and Ventral Hernia Repair; Davol, A Bard Company, 2006; (7 Pages).
The extended European Search Report corresponding to European Application No. EP 12 18 6401.1, completed Nov. 22, 2012 and mailed Nov. 30, 2012; (7 Pages).
The extended European Search Report corresponding to European Application No. EP 12 18 6448.2, completed Nov. 28, 2012 and mailed Dec. 10, 2012; (6 Pages).
The extended European Search Report corresponding to European Application No. EP 12 19 1706.6, completed Dec. 19, 2012 and mailed Jan. 8, 2013; (6 Pages).
The extended European Search Report corresponding to European Application No. EP 11 25 0754.6, completed Oct. 22, 2012 and mailed Oct. 31, 2012; (6 Pages).
European Office Action corresponding to EP 12152989.5, dated May 5, 2015; 4 pp.
Chinese Office Action corresponding to CN 201210015011.8 dated Jan. 4, 2015, with English Translation; (13 pp).

\* cited by examiner

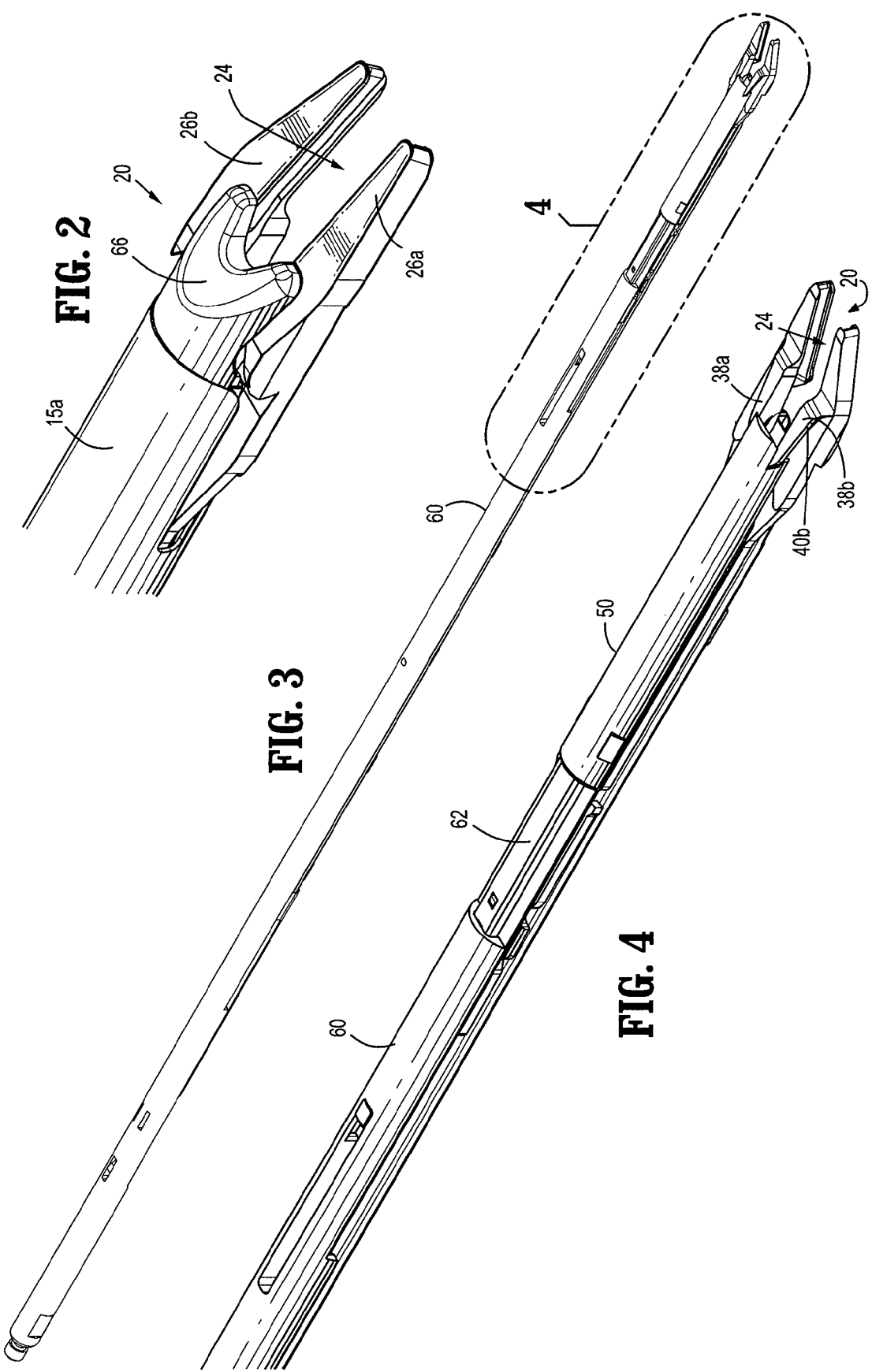

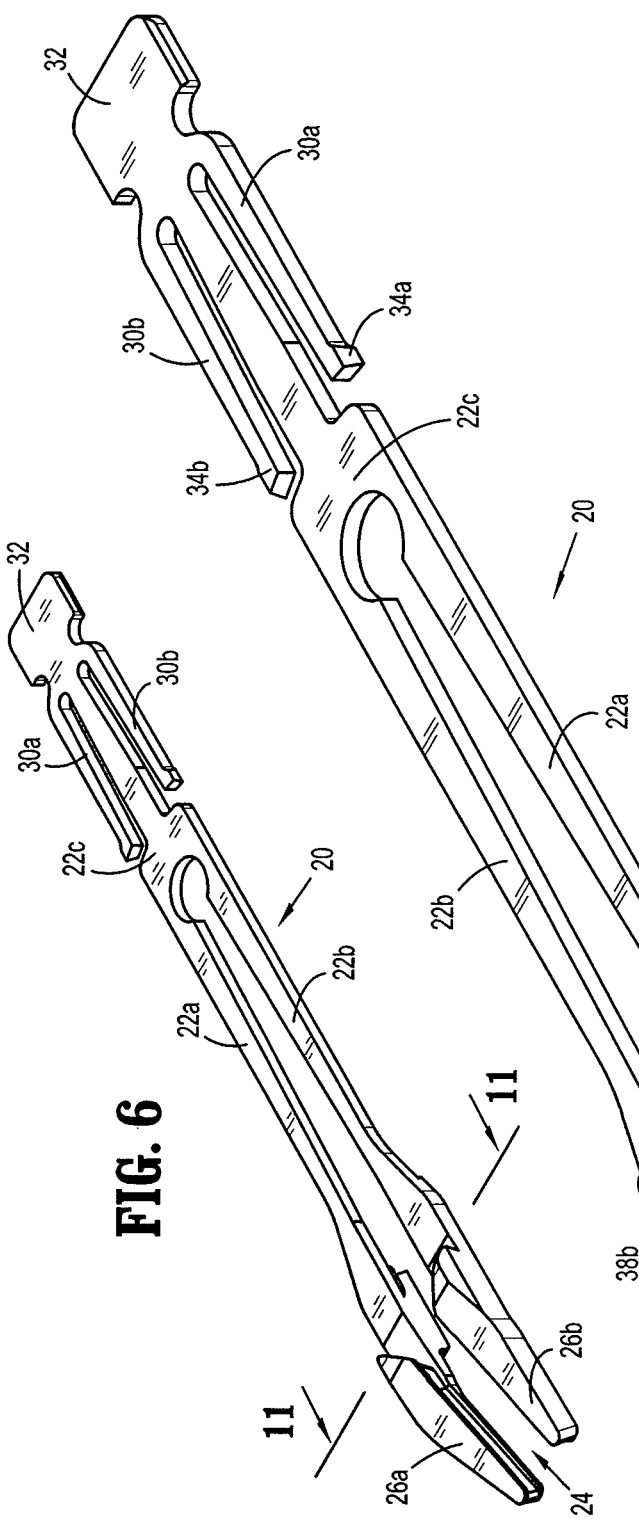

LOCKING CAM DRIVER AND JAW ASSEMBLY FOR CLIP APPLIER

CROSS REFERENCE TO RELATED APPLICATION

The present application claims the benefit of and priority to U.S. Provisional Application Ser. No. 61/438,086, filed on Jan. 31, 2011, the entire contents of which are incorporated herein by reference.

BACKGROUND

1. Technical Field

The present disclosure relates to a clip applier. More particularly, the present disclosure relates to a drive assembly for actuating a jaw assembly of a clip applier.

2. Description of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al., U.S. Pat. No. 5,431,668 to Burbank, III et al., and U.S. Pat. No. 5,700,271 to Whitfield et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Although current clip appliers are effective in applying clips to blood vessels and other various kinds of ducts, it would be beneficial and desirable to provide an endoscopic clip applier having a driving assembly that engages the jaw members in a more secure fashion, for example, to prevent disengagement of the drive assembly from the jaw assembly and/or to prevent clips from twisting during application of the clip.

SUMMARY

The present disclosure relates to an apparatus for endoscopic application of surgical clips to body tissue. The apparatus includes a handle portion, an elongated tubular member, one or more surgical clips, a jaw assembly and a locking cam driver. The elongated tubular member extends distally from the handle portion and defines a longitudinal axis. The surgical clips are disposed within the tubular member.

The jaw assembly includes first and second jaw members that are mounted at a distal end of the elongated tubular member, and define a plane therebetween. Each of the first and second jaw members includes a raised element that has an angled camming surface. The jaw assembly is movable between a spaced, open position and an approximated, substantially closed position.

The locking cam driver includes a bifurcated distal end portion that has a pair of angled camming surfaces. Each of the angled camming surfaces of the locking cam driver is substantially complementary of a respective angled camming surface of the jaw assembly. Further, each of the angled camming surfaces of the locking cam driver is configured to engage a corresponding angled camming surface of the jaw assembly to move the first and second jaw members from the spaced, open position to the approximated, substantially closed position to thereby form a surgical clip.

In embodiments, the locking cam driver may be disposed adjacent to a distal portion of the jaw assembly to cam the jaw members from the spaced, open position to the approximated, substantially closed position.

In other embodiments, the bifurcated distal end portion of the locking cam driver may define a U-shaped space therebetween to gradually cam the first and second jaw members within the locking cam driver upon distal movement thereof.

Each of the angled camming surfaces of the jaw assembly may be disposed on the outer edge of each of the raised elements. Each of the angled camming surfaces of the jaw assembly and the locking cam driver may define a predetermined angle (e.g., an acute angle) relative to the plane defined by the first and second jaw members.

In embodiments, each of the predetermined angles of the angled camming surfaces of the jaw assembly may face toward an outer edge of the jaw assembly and each of the predetermined angles of the angled camming surfaces of the locking cam driver may face toward a center portion of the locking cam driver.

The raised elements may be wider at a distal portion of the jaw members than at a proximal portion of the jaw members so that progressive distal movement of the locking cam driver cams jaw members towards an approximated, closed position.

The angled camming surfaces of locking cam driver and the angled camming surfaces of the jaw assembly may facilitate interlocking of the locking cam driver and the jaw assembly during actuation, and the locking cam driver is drawn towards the jaw assembly to provide greater closure force.

In embodiments, the angle of the angled camming surfaces of the locking cam driver may be different than the angle of the angled camming surfaces of the jaw assembly to provide an offset angled configuration.

In other embodiments, the angle of the angled camming surfaces of the locking cam driver may define a relatively smaller angle than the angle of the angled camming surfaces of the jaw assembly.

The offset angled configuration of the locking cam driver and the jaw assembly may facilitate a pulling of the locking cam driver towards the jaw assembly to provide a greater force while closing the jaw assembly, and to prevent the locking cam driver from disengaging from the jaw assembly during actuation thereof.

The offset angled configuration may reduce surface-to-surface friction between the angled camming surfaces of the locking cam driver and the angled camming surfaces of the jaw assembly.

BRIEF DESCRIPTION OF THE DRAWINGS

Various embodiment of the subject instrument are described herein with reference to the drawings wherein:

FIG. 2 is an enlarged perspective view of a distal end of the clip applier of FIG. 1, illustrating a jaw assembly thereof;

FIG. 3 is a bottom, perspective view of the surgical clip applier of FIG. 1, illustrating a drive assembly including a locking cam driver and the jaw assembly thereof;

FIG. 4 is an enlarged area of detail of FIG. 3;

FIG. 5 is a bottom, perspective view of the jaw assembly shown in an open configuration;

FIG. 6 is a top, perspective view of the jaw assembly of FIG. 5;

DETAILED DESCRIPTION

Figure 1:
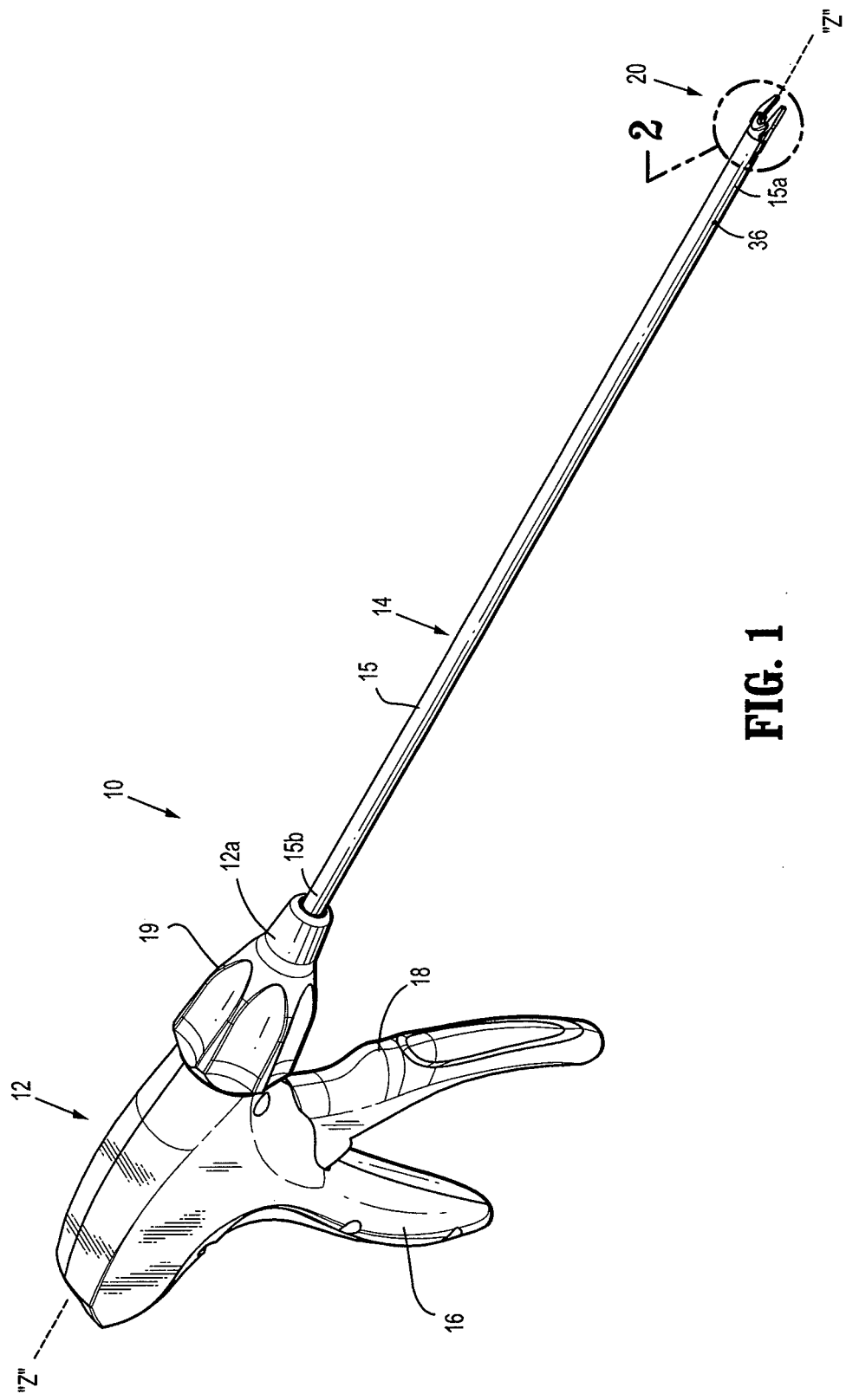
FIG. 1 is a perspective view of a surgical clip applier in accordance with the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

There is disclosed a novel endoscopic surgical clip applier including a drive assembly having, amongst other things, a locking cam driver that is configured to approximate jaw members of a jaw assembly into a substantially closed position. The locking cam driver includes angled camming surfaces that cam along corresponding substantially complementary angled camming surfaces of the jaw assembly. The angled camming surfaces of both the locking cam driver and the jaw assembly are configured to slidingly engage, while locking within each other, in a camming manner. It should be noted that, while the presently disclosed locking cam driver is shown and described with in an endoscopic surgical clip applier, the disclosed locking cam driver and its features may be applicable to any surgical clip applier or any other surgical instrument having a compressible jaw assembly.

Referring now to FIG. 1, a surgical clip applying instrument or surgical clip applier 10 is shown including a handle assembly 12 and an endoscopic portion 14. Endoscopic portion 14 includes an elongated tubular member 15 that extends distally from handle assembly 12. Handle assembly 12 includes a stationary handle 16 and a pivoting or movable handle 18. Manipulation of handle 18 relative to handle 16 actuates a jaw assembly 20, which is operably coupled to a distal end 15a of elongated tubular member 15 or endoscopic portion 14. More specifically, jaw assembly 20 is actuated by a plurality of components of a drive assembly, which will be discussed in more detail below. Handle assembly 12 may be made from any suitable thermoplastic material, and elongated member 15 may be made from any suitable biocompatible material, for example, but not limited to stainless steel, titanium or any suitable plastic material.

In embodiments, a rotating knob 19 is rotatably mounted on a distal end 12a of handle assembly 12. Rotating knob 19 is operably coupled to elongated tubular member 15 of endoscopic portion 14 to provide remote rotation (e.g., 360° of rotation) of elongated tubular member 15 and jaw assembly 20 along a longitudinal center axis "Z-Z" defined by elongated tubular member 15.

Figure 13:
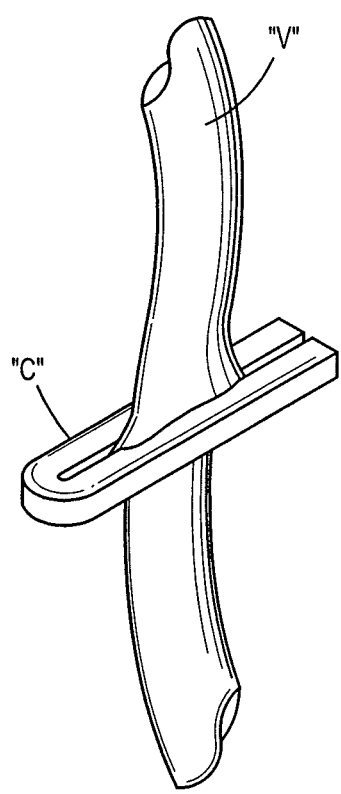
FIG. 13 is a perspective view of a surgical clip formed on a vessel.

Clip applier 10 is configured to retain one or more surgical clips "C" for application to a desired tissue or vessel "V," as shown in FIG. 13. Clip applier 10 has an elongated clip channel member (not shown) that is disposed within elongated tubular member 15 for retaining a number of surgical clips "C." As shown in FIG. 2, clip applier 10 includes a nose 66 to direct the clips "C" traversing through the clip channel member (not shown) into channels 28a and 28b of jaw members 26a and 26b of jaw assembly 20. Jaw assembly 20 and its components will be discussed in greater detail below.

Referring now to FIGS. 3 and 4, the present surgical clip applier 10 includes various components, which will be briefly discussed, in order to actuate jaw assembly 20 to form a closed clip "C" (FIG. 13) therebetween. A detailed discussion of the structure, operation, and method of assembly of various components surgical clip applier 10 is disclosed in commonly owned U.S. Pat. No. 5,700,271 to Whitfield et al., entitled "Apparatus For Applying Surgical Clips" and U.S. Patent Application Publication No. 2006/0085015 to Whitfield et al., entitled "Endoscopic Surgical Clip Applier," the entire contents of each of which is incorporated herein by reference.

In embodiments, clip applier 10 may include a wedging mechanism (not shown) to perform a wedging function that is provided to maintain jaw assembly 20 in a spaced apart condition for loading clip "C" within jaw assembly 20. Once jaw assembly 20 is loaded with clip "C," the wedging mechanism is retracted out of jaw assembly 20 to allow approximation of jaw members 20a and 20b by various components of a drive assembly. In embodiments, clip applier 10 may also include a feeding mechanism (not shown) for feeding a single clip "C" into jaw assembly 20, at a distal portion 15a of elongated tubular member 15, during a single firing stroke of clip applier 10.

Referring still to FIGS. 3 and 4, the drive assembly of surgical clip applier 10 includes an actuation mechanism 60 that operates to pass through the elongated tubular member 15 to thereby actuate a locking cam driver 50 to close jaw assembly 20 and fully form clip "C". More specifically, actuation mechanism 60 is translated in a longitudinally distal and proximal direction through the elongated tubular member 15. A distal portion of actuation mechanism 60 includes a drive assembly having locking cam driver 50 and a slider joint 62 that both extend from the distal end of actuation mechanism 60 to selectively engage camming surfaces 40a and 40b provided on jaw assembly 20, which thereby approximate or close jaw members 26a and 26b around a preloaded surgical clip "C." Actuation mechanism 60 may be operably coupled to locking cam driver 50 via slider joint 62. Actuation mechanism 60, slider joint 62, and locking cam driver 50 are all disposed within elongated tube 15. As will be discussed in greater detail below, actuation of locking cam driver 50 closes the jaw assembly 20 to compress or form a clip "C" that is held therebetween.

With reference to FIGS. 5 and 6, jaw assembly 20 and its components will now be discussed in detail. As discussed above, jaw assembly 20 is positioned on distal end 15a of tubular member 15, and includes juxtaposed jaw members 26a and 26b. Both jaw members 26a and 26b are simultaneously movable between a spaced configuration, in which jaw members 26a and 26b are separated at least a sufficient distance defined by a space 24, to receive a surgical clip "C" therebetween, and an approximated, substantially closed configuration, in which jaw members 26a and 26b are in relatively close relation to one another to form a surgical clip "C" around a vessel "V," as shown in FIG. 13, that has been positioned within surgical clip "C." Each jaw member 26a and 26b has an elongated channel 28a and 28b, respectively, for receipt of a single surgical clip "C" therein. Surgical clip "C" may be applied or placed in elongated channels 28a and 28b by a loading structure of clip applier 10 to apply surgical clip "C" in, for example, a body cavity. Jaw assembly 20 may be made from a suitable biocompatible material, for example, but not limited to stainless steel, titanium or a suitable alloy.

Jaw assembly 20 further includes elongated flexible legs 22a and 22b connected at distal base portion 22c. Flexible legs 22a and 22b are resilient to permit relative approximation and spacing of juxtaposed jaw members 26a and 26b. As discussed above, elongated channels 28a and 28b are provided on or in the juxtaposed inner surfaces of jaw members 26a and 26b for reception of a surgical clip "C."

In an embodiment, jaw assembly 20 may further include locking legs 30a and 30b connected at proximal base portion 34, each having a radially outwardly extending tab 34a and 34b, respectively, formed thereon. Tabs 34a and 34b are configured to engage corresponding holes 36 defined on elongated tube 15 (FIG. 1) to secure jaw assembly 20 to elongated tube 15. It is contemplated that jaw assembly 20 may be secured to elongated 15 in any manner known by one having skill in the art.

As depicted in FIG. 5, each of jaw members 26a and 26b includes raised elements 38a and 38b, respectively, formed on a bottom surface thereof. In order to provide increased closing force, camming surfaces 40a and 40b are disposed on an outer surface of each of raised elements 38a and 38b, respectively, to facilitate closure of jaw members 26a and 26b of jaw assembly 20. Camming surfaces 40a and 40b each define an angle "β" relative to a horizontal axis "X-X" defined by jaw members 26a and 26b (FIG. 11) to correspond with substantially complementary angled camming surfaces of locking cam driver 50, which will be described in greater detail below.

Figure 7:
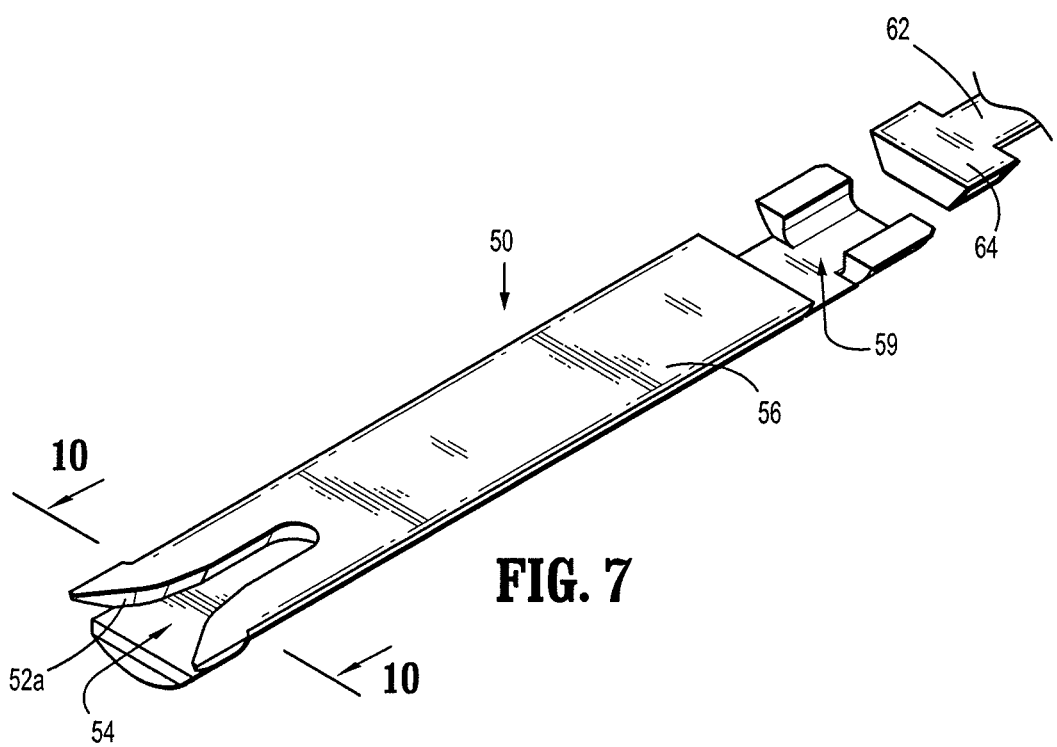
FIGS. 7 and 8 are front, perspective views of the locking cam driver illustrated in FIGS. 3 and 4.
Figure 8:
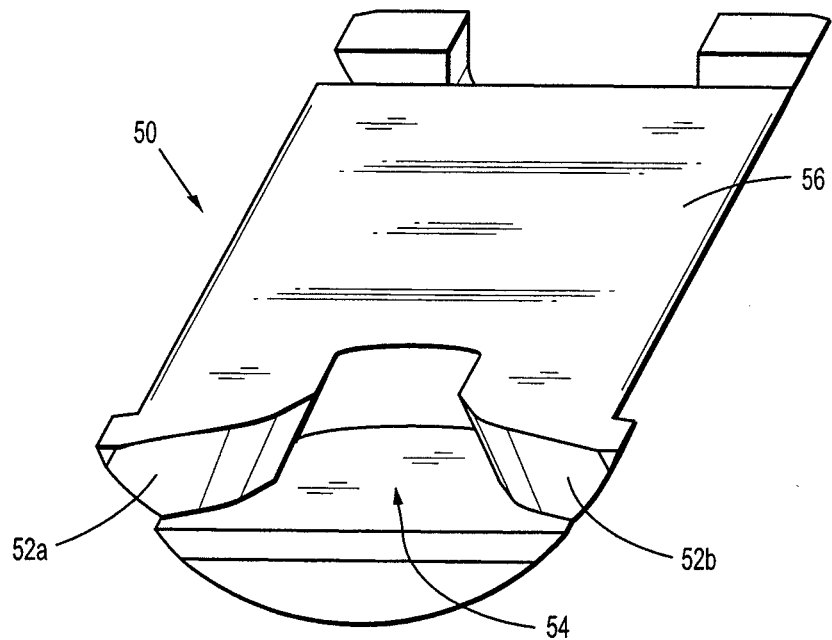
Figure 9:
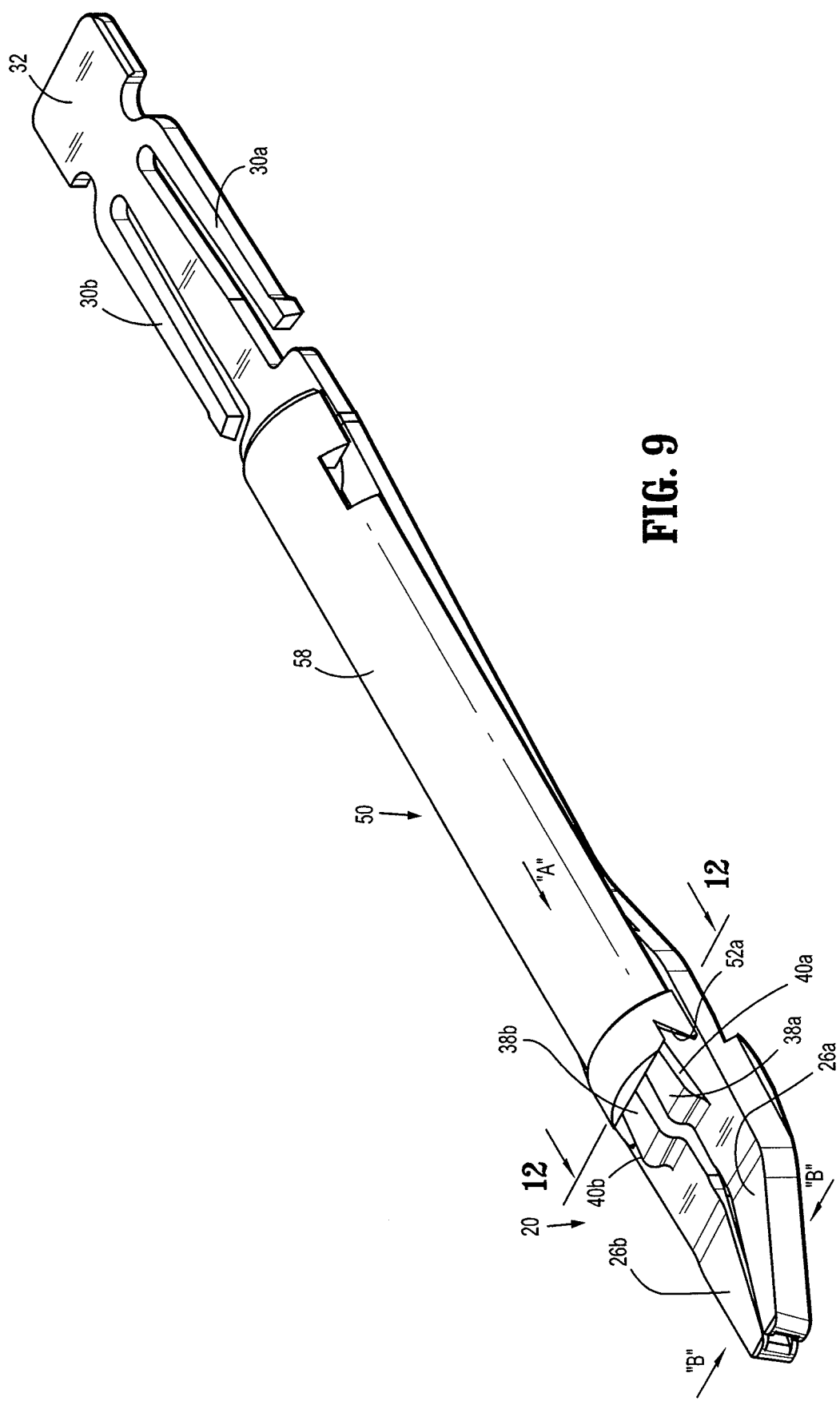
FIG. 9 is a bottom, perspective view illustrating the locking cam driver assembly actuating the jaw assembly to an approximated, substantially closed configuration.

Turning now to FIGS. 7 and 8, locking cam driver 50 has a hemispherical configuration that includes a flat, top surface 56 that engages (or is adjacent) jaw assembly 20 and a curved portion (e.g., semi-circular) 58 (FIG. 9) that engages (or is adjacent) an inner portion of elongated tubular member 15.

At a proximal portion, locking cam driver 50 includes a T-shaped recess 59 that is configured to receive a distal T-shaped end 64 of slider joint 62. It should be noted that other types of connecting configurations may be utilized to connect locking cam driver 50 to slider joint 62. For example, locking cam driver 50 may be connected to slider joint 62 by crimping, welding, bolting, and adhering.

At a distal portion, locking cam driver 50 includes a bifurcated configuration having a pair of spaced apart angled camming surfaces 52a and 52b that surround and define a U-shaped space 54 that is dimensioned and configured to receive corresponding substantially complementary angled camming surfaces 40a and 40b of jaw assembly 20. More particularly, distal movement of locking cam driver 50 moves camming surfaces 52a and 52b thereof with respect to and against camming surfaces 40a and 40b of raised elements 38a and 38b to thereby move jaw members 26a and 26b from the un-approximated, open position into the approximated, substantially closed position. When jaw members 26a and 26b are moved to the approximated, substantially closed position, a clip "C" is formed when positioned within elongated channels 28a and 28b of jaw assembly 20, as shown in FIG. 13.

Referring now to FIGS. 9-12, during use, handle 18 of handle assembly 12 (FIG. 1) is actuated toward handle 16, to a closed position. During actuation of handle 18, the driving assembly of clip applier 10 moves actuation mechanism 60, slider joint 62, and locking cam driver 50 in a distal direction, as depicted by directional arrow "A" of FIG. 9.

As discussed above, during distal movement of locking cam driver 50 relative to jaw assembly 20, camming surfaces 52a and 52b of locking cam driver 50 engage camming surfaces 40a and 40b of jaw members 26a and 26b. In this manner, jaw members 26a and 26b are gradually brought into approximation with distal movement of locking cam driver 50. More particularly, since raised elements 38a and 38b are wider at the distal portion than at the proximal portion, progressive distal movement of U-shaped locking cam driver 50 cams jaw members 26a and 26b towards an approximated, closed position, as depicted by direction arrows "B" of FIG. 9. The proximity of locking cam driver 50 and raised elements 38a and 38b to the distal portion of jaw members 26a and 26b enables sufficient force to be exerted on jaw members 26a and 26b to deform clip "C" and compress blood vessels or other body tissue surrounded thereby.

Figure 10:
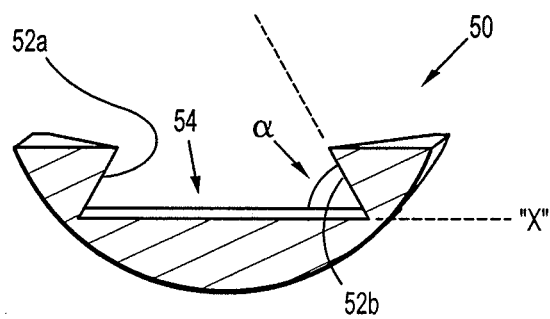
FIG. 10 is a front, cross-sectional, perspective view of the locking cam driver taken along lines 10-10, as shown in FIG. 7.
Figure 11:
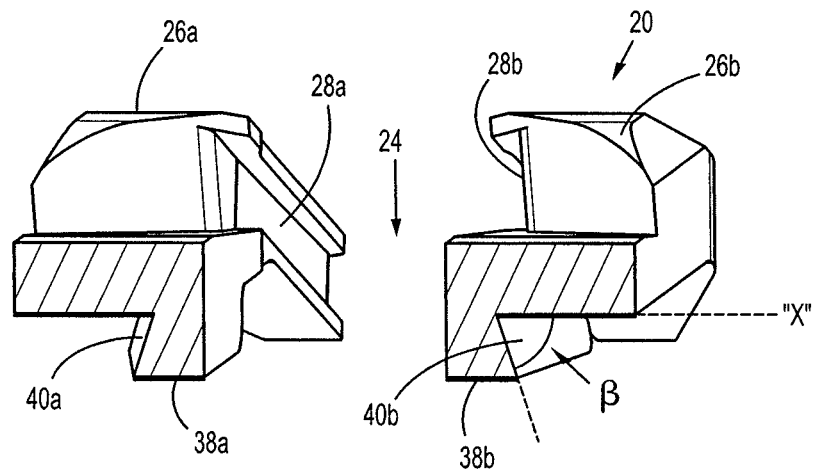
FIG. 11 is a front, cross-sectional, perspective view the jaw assembly taken along lines 11-11, as shown in FIG. 6.
Figure 12:
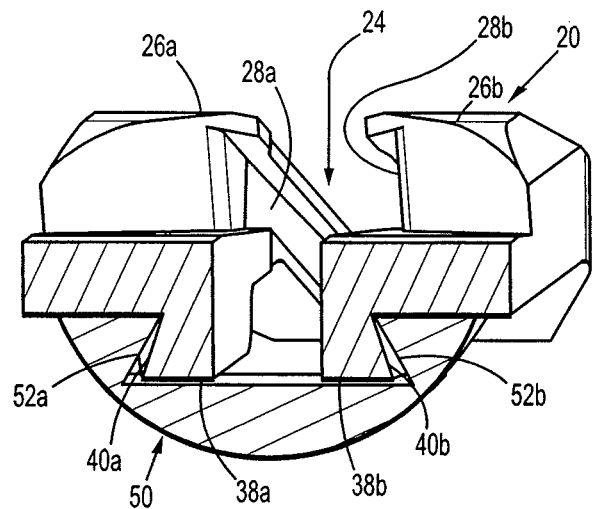
FIG. 12 is a front, cross-sectional, perspective view illustrating the locking cam driver actuating the jaw assembly taken along lines 12-12, as shown in FIG. 9.

Turning now specifically to FIGS. 10-12, and initially to FIG. 10, camming surfaces 52a and 52b of locking cam driver 50 are configured to define predetermined acute angles "α" relative to a horizontal plane defined by axes "X-X" and "Z-Z." Camming surfaces 52a and 52b form predetermined acute angles "α" oriented towards space 54 (e.g., towards a center of locking cam driver 50) to provide a capturing configuration. As shown in FIG. 11, calming surfaces 40a and 40b of raised elements 38a and 38b of jaw members 26a and 26b are configured to define predetermined acute angles "β" relative to a horizontal plane defined by axes "X-X" and "Z-Z." In an opposite manner, with comparison to camming surfaces 52a and 52b of locking cam driver 50, camming surfaces 40a and 40b of raised elements 38a and 38b form predetermined acute angles "β" oriented towards an outer edge of jaw assembly 20 (e.g., away from the center of jaw assembly 20). In accordance with the present disclosure, the plane defined by axes "X-X" and "Z-Z" may also be represented by the plane defined by flexible legs 22a and 22b of jaw assembly 20 and/or by top surface 56 of locking cam driver 50.

During actuation of locking cam driver 50 along the jaw assembly 20, as depicted in FIG. 12, the angled camming surfaces 52a and 52b of locking cam driver 50 engage and lock with corresponding angled camming surfaces 40a and 40b to prevent locking cam driver 50 from disengaging from jaw assembly 20. By providing angled camming surfaces 52a and 52b of locking cam driver 50 and angled camming surfaces 40a and 40b of jaw assembly 20, locking cam driver 50 and jaw assembly 20 interlock with each other so that during actuation, locking cam driver 50 is drawn towards jaw assembly 20 to provide more closure force. The angled configuration also maintains jaw members 26a and 26b in alignment with each other (e.g., along the "X-X" axis), which prevents clips "C" from twisting during formation.

In embodiments, predetermined angles "α" of camming surfaces 52a and 52b of locking cam driver 50 and predetermined angles "β" of camming surfaces 40a and 40b of jaw assembly 20 may have different degree values to provide an offset angled configuration. More particularly, predetermined angles "α" may be a relatively smaller angle (e.g., 30 degrees) than predetermined angles "β" (e.g., 45 degrees). The offset angled configuration facilitates pulling of the locking cam driver 50 towards jaw assembly 20 to provide a greater force while closing jaw assembly 20 and to prevent locking cam driver 50 from disengaging from jaw assembly 20 during actuation. The offset angled configuration also reduces surface-to-surface friction between camming surfaces 40a and 40b and camming surfaces 52a and 52b, respectively, since the planes of each corresponding camming surfaces are offset because of the difference in the degree values for angles "α" and "β."

During a manufacturing process, the angled camming surfaces 40a and 40b of respective jaw members 26a and 26b can be machined in a one-step process. More particularly, an angled cutter head may be used to cut the angled camming surface 40a and 40b along the side of raised elements 38a and 38b, respectively.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed:

1. An apparatus for endoscopic application of surgical clips to body tissue, the apparatus comprising:
   a handle portion;
   an elongated tubular member extending distally from the handle portion and defining a longitudinal axis;
   at least one surgical clip disposed within the tubular member;
   a jaw assembly including first and second jaw members mounted at a distal end of the elongated tubular member, the first and second jaw members defining a plane therebetween, each of the first and second jaw members including a raised element having an angled camming surface, the jaw assembly being movable between a spaced, open position and an approximated, substantially closed position; and
   a locking cam driver including a bifurcated distal end portion having a pair of angled camming surfaces, wherein the angle of the angled camming surfaces of the locking cam driver is different than an angle of a respective angled camming surface of the jaw assembly to provide an offset angled configuration, wherein each angled camming surface of the locking cam driver is substantially complementary of the respective angled camming surface of the jaw assembly, each angled camming surface of the locking cam driver configured to engage a corresponding angled camming surface of the jaw assembly to move the first and second jaw members from the spaced, open position to the approximated, substantially closed position to thereby form a surgical clip.

2. The apparatus according to claim 1, wherein the locking cam driver is disposed adjacent to a distal portion of the jaw assembly to cam the jaw members from the spaced, open position to the approximated, substantially closed position.

3. The apparatus according to claim 1, wherein the raised elements are disposed on a surface of the jaw members facing the locking cam driver.

4. The apparatus according to claim 1, wherein the bifurcated distal end portion of the locking cam driver defines a U-shaped space therebetween to gradually cam the first and second jaw members within the locking cam driver upon distal movement thereof.

5. The apparatus according to claim 4, wherein distal movement of the locking cam driver moves the angled camming surfaces of the jaw assembly into the U-shaped space with respect to the angled camming surfaces of the locking cam driver to thereby move the jaw members into the approximated, substantially closed position.

6. The apparatus according to claim 1, wherein each of the angled camming surfaces of the jaw assembly are disposed on an outer edge of each of the raised elements.

7. The apparatus according to claim 1, wherein each of the angled camming surfaces of the jaw assembly and the locking cam driver defines a predetermined angle relative to the plane defined by the first and second jaw members.

8. The apparatus according to claim 7, wherein each of the predetermined angles of the angled camming surfaces of the jaw assembly and the locking cam driver defines an acute angle with respect to the plane defined by the first and second jaw members.

9. The apparatus according to claim 7, wherein each of the predetermined angles of the angled camming surfaces of the jaw assembly face toward an outer edge of the jaw assembly.

10. The apparatus according to claim 7, wherein each of the predetermined angles of the angled camming surfaces of the locking cam driver face toward a center portion of the locking cam driver.

11. The apparatus according to claim 1, wherein the raised elements are wider at a distal portion of the jaw members than at a proximal portion of the jaw members so that progressive distal movement of the locking cam driver cams jaw members towards the approximated, closed position.

12. The apparatus according to claim 1, wherein the angled camming surfaces of locking cam driver and the angled camming surfaces of the jaw assembly facilitates interlocking of the locking cam driver and the jaw assembly during actuation, and the locking cam driver is drawn towards the jaw assembly to provide greater closure force.

13. The apparatus according to claim 1, wherein the angle of the angled camming surfaces of the locking cam driver defines a relatively smaller angle than the angle of the angled camming surfaces of the jaw assembly.

14. The apparatus according to claim 1, wherein the offset angled configuration of the locking cam driver and the jaw assembly facilitates a pulling of the locking cam driver towards the jaw assembly to provide a greater force while closing the jaw assembly, and to prevent the locking cam driver from disengaging from the jaw assembly during actuation thereof.

15. The apparatus according to claim 1, wherein the offset angled configuration reduces surface-to-surface friction between the angled camming surfaces of the locking cam driver and the angled camming surfaces of the jaw assembly.

* * * * *